United States Patent
Geissler et al.

(10) Patent No.: US 6,194,627 B1
(45) Date of Patent: Feb. 27, 2001

(54) PROCESS FOR PREPARING AROMATIC OLEFINS BY USING PALLADAPHOSPHACYCLOBUTANES AS CATALYSTS

(75) Inventors: Holger Geissler, Mainz; Peter Gross, Kelsterbach; Bianca Guckes, Waldems; Michael Klimpel, Bad Reichenhall, all of (DE)

(73) Assignee: Aventis Research & Technology GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/308,189

(22) PCT Filed: Nov. 13, 1997

(86) PCT No.: PCT/EP97/06328

§ 371 Date: Aug. 20, 1999

§ 102(e) Date: Aug. 20, 1999

(87) PCT Pub. No.: WO98/22412

PCT Pub. Date: May 28, 1998

(30) Foreign Application Priority Data

Nov. 18, 1996 (DE) .............................................. 196 47 582

(51) Int. Cl.⁷ .......................... C07C 1/207; C07C 15/46; C07C 5/09
(52) U.S. Cl. .......................... 585/436; 585/435; 585/438
(58) Field of Search .................................. 585/436, 435, 585/466, 469, 438

(56) References Cited

U.S. PATENT DOCUMENTS 5,698,755   12/1997   Beller et al. .......................... 585/466
6,005,151 * 12/1999   Herrmann et al. .................... 585/438

FOREIGN PATENT DOCUMENTS 44 21 730 C1   11/1995   (DE) .
0 725 049 A1    8/1996   (EP) .

OTHER PUBLICATIONS

Herrmann et al., "Palladacycles as Structurally Defined Catalysts for the Heck Olefination of Chloro– and Bromoarenes", Angewandte Chemie International Edition, vol. 34, No. 17, Sep. 15, 1995, pp. 1844–1848.

* cited by examiner

Primary Examiner—Marian C. Knode
Assistant Examiner—Thuan D. Dang
(74) Attorney, Agent, or Firm—Frommer Lawrence & Haug

(57) ABSTRACT

The invention relates to a process for preparing monofunctional, bifunctional and polyfunctional aromatic olefins of the formula (I)

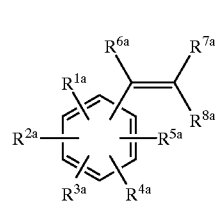

(I)

by reacting haloaromatics of the formula (II)

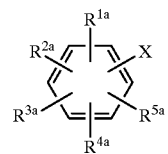

(II)

with olefins of the formula (III)

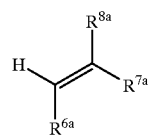

(III)

wherein a palladium compound of the formula (IV)

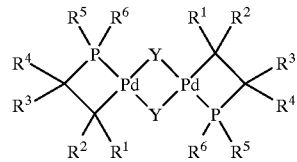

is used as catalyst.

16 Claims, No Drawings

PROCESS FOR PREPARING AROMATIC OLEFINS BY USING PALLADAPHOSPHACYCLOBUTANES AS CATALYSTS

The present invention relates to a new process for preparing aromatic olefins using palladaphosphacyclobutanes as novel catalysts.

Aromatic olefins, in particular cinnamic acid derivatives, styrenes and stilbenes are industrially important as fine chemicals, starting materials for polymers, UV absorbers and precursors for syntheses.

A frequently employed method of synthesizing aromatic olefins on a laboratory scale is the Heck reaction in which iodoaromatics or bromoaromatics and in exceptional cases chloroaromatics are reacted with olefins in the presence of palladium catalysts. Reviews which describe this method may be found in R. F. Heck, Acc. Chem. Res. 1979, 12, 146; R. F. Heck, Org. React. 1982, 27, 345; R. F. Heck, Palladium Reagents in Synthesis, Academic Press, London 1985.

The catalysts which are used for the Heck reaction are palladium compounds. Although both palladium(II) and palladium(0) complexes can be used in Heck reactions, it is generally accepted that only palladium(0) compounds are the actual catalysts in the reaction. In particular, coordinatively unsaturated 14-electron palladium(0) species which are generally stabilized with weak donor ligands such as phosphines are formulated in the literature.

Despite the many publications on the subject of the Heck reaction, only a few examples of an industrial application of this method are known to the present time. This is attributable to the fact that the catalyst systems described frequently give satisfactory catalytic turnover numbers only with uneconomical starting materials such as iodoaromatics. Otherwise, in the case of bromoaromatics and particularly in the case of chloroaromatics, it is generally necessary to add large amounts of catalyst, usually 1–5 mol %, in order to achieve industrially useful conversions. In addition, owing to the complexity of the reaction mixtures, no simple catalyst recycling is possible, so that the catalyst costs also generally stand in the way of industrial implementation.

DE-4421730 discloses the hitherto best process using palladaphosphaindanes, known as palladacycles, for the Heck reaction. It comprises the reaction of bromoaromatics and chloroaromatics with olefins. Activated bromoaromatics, for example 4-bromoacetophenone, 4-bromobenzaldehyde or 4-iodobromobenzene, are reacted in yields of up to 100% using amounts of from 0.002 to 0.01 mol % of palladium catalyst in the form of palladaphosphaindane. Less active bromoaromatics, for example bromotoluene or bromobenzene, are reacted in yields of up to 96% using amounts of 2 mol % of palladium as catalyst in the form of palladaphosphaindane. In the reaction of activated chloroaromatics, for example chloroacetophenone, it is necessary to add halide ions in the form of their salts, for example lithium bromide, in order to achieve high yields. Thus, the reaction of 100 mmol of 4-chloroacetophenone, 170 mmol of 2-ethylhexyl acrylate, 110 mmol of sodium acetate, 10 mmol of lithium, bromide in 100 ml of dimethylacetamide with 0.05 mmol of di-$\mu$-acetato-bis(o-(di-o-tolylphosphino)benzyl)dipalladium(II) (corresponds to 0.1 mol % of palladium) as catalyst gives a yield of 82% of 2-ethylhexyl trans-4-acetylcinnamate after 18 hours at 130° C. Since, owing to the complexity of the reaction mixtures, simple catalyst recycling is not possible when using palladaphosphaindanes either, the catalyst costs generally stand in the way of industrial implementation in the case of the less active bromoaromatics and chloroaromatics. In addition, in the case of the chloroaromatics, the addition of halides or pseudo halides is ecologically disadvantageous, especially since these do not contribute to the reaction but only serve to stabilize the palladaphosphaindanes.

There is therefore a need for a process which does not have the abovementioned disadvantages, is suitable for carrying out in industry and gives aromatic olefins in high yield and purity.

The invention provides a process for preparing aromatic olefins of the formula (I)

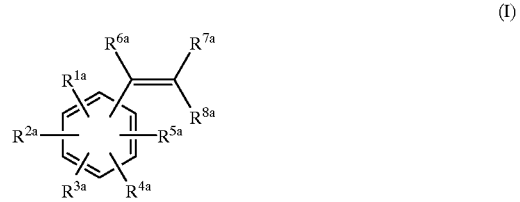

(I)

where
$R^{1a}$ to $R^{5a}$ are, independently of one another, hydrogen, $C_1$–$C_8$-alkyl, $C_1$–$C_8$-alkoxy, $C_1$–$C_8$-acyloxy, O-phenyl, phenyl, fluorine, chlorine, bromine, OH, $NO_2$, $OSO_2CF_3$, CN, COOH, CHO, $SO_3H$, $SO_2R$, SOR, $NH_2$, NH—$C_1$–$C_8$-alkyl, $N(C_1$–$C_8$-alkyl$)_2$, $CHal_3$, NHCO—$C_1$–$C_4$-alkyl, N—$C_1$–$C_4$-alkyl-CO—$C_1$–$C_4$-alkyl, COO—$C_1$–$C_8$-alkyl, $CONH_2$, CO—$C_1$–$C_8$-alkyl, NHCOH, NCOO—$C_1$–$C_4$-alkyl, CO-phenyl, COO-phenyl, CHCH—$CO_2$—$C_1$–$C_8$-alkyl, $CHCHCO_2H$, PO(phenyl$)_2$, PO($C_1$–$C_4$-alkyl$)_2$, $OSO_2$-phenyl, $OSO_2CH_3$, where one of the radicals $R^{1a}$ to $R^{5a}$ can also be

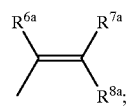

$R^{6a}$ is hydrogen, $C_1$–$C_8$-alkyl, phenyl, O—$C_1$–$C_8$-alkyl, fluorine;
$R^{7a}$ and $R^{8a}$ are, independently of one another, hydrogen, CN, $CO_2H$, $CO_2$—$C_1$–$C_8$-alkyl, $CONH_2$, CONH—$C_1$–$C_4$-alkyl, CON($C_1$–$C_4$-alkyl$)_2$, fluorine, $CO_2$-phenyl, $C_1$–$C_8$-phenyl, PO(phenyl$)_2$, PO($C_1$–$C_4$-alkyl$)_2$, CO-phenyl, CO—$C_1$–$C_4$-alkyl, O—$C_1$–$C_4$-alkyl, NH—$C_1$–$C_4$-alkyl, $PO_3H$, $SO_3H$, $SO_3$—$C_1$–$C_4$-alkyl, $SO_2$—$C_1$–$C_4$-alkyl, O-phenyl, $C_1$–$C_8$-alkyl,
$R^3$, $R^4$, $R^5$, $R^6$ are, independently of one another, $C_1$–$C_8$-alkyl, $C_3$–$C_{12}$-cycloalkyl, aryl;
or where $R^1$ and $R^2$, $R^1$ or $R^2$ and $R^3$ or $R^4$, $R^3$ and $R^4$, $R^3$ or $R^4$ and $R^5$ or $R^6$, $R^5$ and $R^6$ together form an aliphatic ring having from 4 to 10 carbon atoms,
or where $R^5$ and $R^6$, $R^3$ or $R^4$ and $R^5$ or $R^6$ together form an aromatic ring having from 5 to 9 carbon atoms, and
Y is an anion of an inorganic or organic acid,
is used as catalyst.

The process is preferably carried out using compounds of the formula (IV) in which
$R^1$, $R^2$ are, independently of one another, phenyl,
$R^5$, $R^6$ are, independently of one another, phenyl, naphthyl, anthracenyl which may each be substituted by from 1 to 3 $C_1$–$C_4$-alkyl or from 1 to 3 $C_1$–$C_4$-alkoxy groups, and
Y is acetate, propionate, benzoate, chloride, bromide, iodide, fluoride, sulfate, hydrogensulfate, nitrate, phosphate, tosylate, mesylate, trifluoromethanesulfonate, tetrafluoroborate, acetylacetonate, hexafluoroacetylacetonate or pyrazolyl.

The process is particularly preferably carried out using compounds of the formula (IV) in which $R^5$, $R^6$ are, independently of one another, o-trifluoromethylphenyl, o-trifluoromethyl-p-tolyl, o-trifluoromethyl-p-methoxyphenyl, o-methoxyphenyl, o,p-dimethoxyphenyl, o,o,p-trimethoxyphenyl, anthracenyl, tert-butyl, n-butyl, isopropyl, isobutyl, cyclohexyl, 1-methylcyclohexyl.

In particular, the compounds di-$\mu$-acetato-bis[2-[bis(1,1-dimethylethyl)phosphino]-2-methylpropyl-C,P]dipalladium(II)

di-$\mu$-acetato-bis[2-[(1,1-dimethylethyl)phenylphosphino]-2-methylpropyl-C,P]dipalladium(II)

di-$\mu$-chloro-bis[2-[bis(1,1-dimethylethyl)phosphino]-2-methylpropyl-C,P]dipalladium(II)

di-$\mu$-chloro-bis[2-[(1,1-dimethylethyl)phenylphosphino]-2-methylpropyl-C,P]dipalladium(II)

di-$\mu$-bromo-bis[2-[bis(1,1-dimethylethyl)phosphino]-2-methylpropyl-C,P]dipalladium(II)

di-$\mu$-bromo-bis[2-[(1,1-dimethylethyl)phenylphosphino]-2-methylpropyl-C,P]dipalladium(II)

are used for the process.

As solvents, use is generally made of inert organic solvents. Well suited solvents are dipolar aprotic solvents such as dialkyl sulfoxides, N,N-dialkylamides of aliphatic carboxylic acids or alkylated lactams. Preference is given to dimethyl sulfoxide, dimethylacetamide, dimethylformamide and N-methylpyrrolidone.

The reaction proceeds at temperatures of from 20 to 200° C.; in many cases it has been found to be useful to carry it out at temperatures of from 60 to 180° C., preferably from 80 to 150° C.

Since HX is eliminated in the reaction, it is advantageous to neutralize this acid by addition of a base. Suitable bases are primary, secondary or tertiary amines such as alkylamines, dialkylamines, trialkylamines, each of which may be alicyclic or open-chain, alkali metal or alkaline earth metal salts of aliphatic or aromatic carboxylic acids or of carbonic acid, for example lithium, sodium, potassium, calcium or magnesium acetate and corresponding carbonates or hydrogencarbonates and oxides or hydroxides of the alkali or alkaline earth metals, for example lithium, magnesium or calcium hydroxide and calcium or magnesium oxide. All bases can likewise be used in the form of water-containing compounds which has the advantage that it is possible to use base which are difficult to prepare in water-free form.

The palladium catalysts used are generally synthesized and isolated before the actual reaction, but they can also be generated in situ without the initial catalytic activity being reduced thereby. However, in the case of a relatively long reaction procedure, the mixtures generate in situ (molar ratio Pd:P=1:1) are found to be less stable and frequently lead to precipitation of palladium. In the case of in situ mixtures, it is therefore necessary to employ an excess of phosphine, which is not needed when using the palladaphosphacyclobutanes.

The palladaphosphacyclobutanes which are used or formed generally have a dimeric structure. However, in the case of certain compounds (e.g. Y=acetylacetone, hexafluoroacetylacetone) monomeric, oligomeric or polymeric structures can also be present.

During the catalysis cycle, bridge cleavage reactions with inorganic and organic nucleophiles break up the dimeric structure, so that the actual catalytically active species are considered to be the mononuclear complexes of the formula (V) or (VI)

(V)

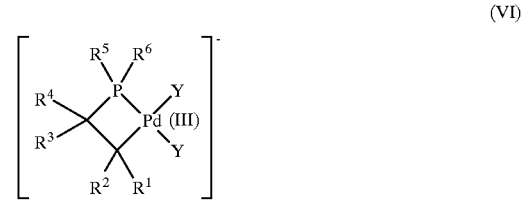

(VI)

The complexes of the formulae (V) and (VI) are in equilibrium with the dimers actually used and have a neutral or anionic character. The mononuclear complex of the formula (V) may have further donor ligands on the palladium atom.

The very advantageous course of the reaction of the invention was particularly surprising since the prior art does not describe palladium catalysts of the formula (IV) for carrying out the Heck reaction.

The palladaphosphacyclobutanes used as new catalyst systems have a very high activity and unexpectedly high stability.

The stability of the palladaphosphacyclobutanes in solution can be increased by addition of salts of alkali metals, alkaline earth metals and transition metals of transition groups VI to VII. In particular, the addition of halides and pseudo halides (e.g. CN$^-$) effect significant yield increases (1–100%) and improvements in the operating life of the catalyst in the reaction of chloroaromatics. Trialkylammonium and tetraalkylammonium salts as well as the corresponding phosphonium and arsonium salts are also suitable as stabilizing additives.

Turnover numbers in the order of 1,000,000 and more can be achieved.

Owing to the activity and stability of the catalyst, it is thus possible in certain processes to use extremely small amounts of catalyst, so that the catalyst costs are very low compared to the prior art.

In addition, the use of very small amounts of catalyst gives ecological advantages, since waste products or waste-producing work-up processes are avoided.

The following examples illustrate the process of the invention.

EXAMPLE 1

Synthesis of the Catalyst

Di-$\mu$-acetato-bis[2-[bis(1,1-dimethylethyl)phosphino]-2-methylpropyl-C,P]dipalladium(II)

5.10 g (22.7 mmol) of Pd(OAc)$_2$ are dissolved in 200 ml of toluene to give a reddish brown solution. The solution is admixed with 5.00 mg (24.7 mmol) of tri(tert-butyl)phosphine. The solution which clears rapidly to a light orange color is heated at 70–80° C. for 10 minutes and then cooled to room temperature. The solvent is removed under reduced pressure. After addition of 200 ml of hexane, the product, di-μ-acetato-bis[2-[bis(1,1-dimethylethyl)phosphino]-2-methylpropyl-C,P]dipalladium, crystallizes out after a short time and is filtered off. This gives 6.65 g (80% of theory), based on Pd(OAc)$_2$ of product as a whitish yellow solid (m.p.>200° C.). Recrystallization from hexane and filtration of the solutions through Celite® enables the product to be obtained analytically pure in the form of whitish yellow crystalline needles.

Elemental analysis: C$_{28}$H$_{58}$O$_4$P$_2$Pd$_2$ (733.51): found: C, 45.6%; H, 7.7%; calc.: C, 45.85%; H, 7.97%;

$^1$H-NMR (300 MHz, CDCl$_3$): d=1.88 (3H, s, CH$_3$); 1.50 (d, 18H, CH$_3$, $^4$J(PH)=14 Hz); 1.44 (d, 12H, CH$_3$, $^4$J(PH)=15 Hz); 1.07 (2H, s$_{broad}$, 4H, CH$_2$); $^{13}$C{$^1$H}-NMR (75.4 MHz, −70 C, CD$_2$Cl$_2$): d=181.5 (s, CH$_3$$\underline{C}$O$_2$); 49.5 (s, P$\underline{C}$, J(PC)=20.1 Hz); 37.5 (s, P$\underline{C}$, J(PC)=10.6 Hz); 32.3 (s, $\underline{C}$H$_3$, J(PC)=2.9 Hz); 31.1 (s, $\underline{C}$H$_3$); 24.7 (s, $\underline{C}$H$_3$CO$_2$); 7.2 (s, $\underline{C}$H$_2$, J(PC)=33.6 Hz). $^{31}$P{$^1$H}-NMR (121.4 MHz, CDCl$_3$): =−8.5 (s).

COMPARATIVE EXAMPLE 1

16 mmol of 4-bromoanisole, 21 mmol of n-butyl acrylate and 18 mmol of potassium carbonate are stirred for 16 hours at 140° C. in 10 ml of dimethylacetamide with 0.08 μmol of di-μ-acetato-bis[-o-(di-o-tolylphosphino)benzyl]dipalladium(II) as catalyst.

Yield: 17.7% of n-butyl 4-methoxycinnamate (GC analysis).

COMPARATIVE EXAMPLE 2

16 mmol of 4-bromoanisole, 21 mmol of n-butyl acrylate and 18 mmol of potassium carbonate are stirred for 17 hours at 140° C. in 10 ml of dimethylacetamide with 0.16 μmol of palladium acetate and 0.16 μmol of tri(tert-butyl)phosphine as catalyst.

Yield: 13.8% of n-butyl 4-methoxycinnamate (GC analysis).

EXAMPLE 2

16 mmol of 4-bromoanisole, 21 mmol of n-butyl acrylate and 18 mmol of potassium carbonate are stirred for 16 hours at 140° C. in 10 ml of dimethylacetamide with 0.08 μmol of di-μ-acetato-bis[2-[bis(1,1-dimethylethyl)phosphino]-2-methylpropyl-C,P]dipalladium(II) as catalyst.

Yield: 89.9% of n-butyl 4-methoxycinnamate (GC analysis).

COMPARATIVE EXAMPLE 3

16 mmol of 4-bromoanisole, 21 mmol of n-butyl acrylate and 18 mmol of potassium carbonate are stirred for 17 hours at 140° C. in 10 ml of dimethylacetamide with 1.6 μmol of palladium acetate and 1.6 μmol of tri(tert-butyl)phosphine as catalyst.

Yield: 45.2% of n-butyl 4-methoxycinnamate (GC analysis).

EXAMPLE 3

16 mmol of 4-bromoanisole, 21 mmol of n-butyl acrylate and 18 mmol of potassium carbonate are stirred for 24 hours at 140° C. in 10 ml of dimethylacetamide with 0.8 μmol of di-μ-acetato-bis[2-[bis(1,1 -dimethylethyl)phosphino]-2-methylpropyl-C,P]dipalladium(II) as catalyst.

Yield: 99.2% of n-butyl 4-methoxycinnamate (GC analysis).

COMPARATIVE EXAMPLE 4

10 mmol of 4-chlorobenzaldehyde, 15 mmol of n-butylacrylate, 15 mmol of sodium acetate and 2 mmol of tetrabutylammonium bromide are stirred for 4 hours at 140° C. in 10 ml of dimethylacetamide with 0.01 mmol of di-μ-acetato-bis[o-(di-o-tolylphosphino)benzyl]dipalladium (II) as catalyst.

Yield: 35.2% of butyl 4-formylcinnamate (GC analysis).

EXAMPLE 4

10 mmol of 4-chlorobenzaldehyde, 15 mmol of n-butyl acrylate, 15 mmol of sodium acetate and 2 mmol of tetrabutylammonium bromide are stirred for 4 hours at 140° C. in 10 ml of dimethylacetamide with 0.01 mmol of di-μ-chloro-bis[2-[bis(1,1-dimethylethyl)phosphino]-2-methylpropyl-C,P]dipalladium(II) as catalyst.

Yield: 71.7% of butyl 4-formylcinnamate (GC analysis).

COMPARATIVE EXAMPLE 5

20 mmol of bromobenzene, 25 mmol of n-butyl acrylate and 25 mmol of potassium carbonate are stirred for 2 hours at 140° C. in 20 ml of dimethylacetamide with 1.0 μmol of di-μ-acetato-bis[-o-(di-o-tolylphosphino)benzyl]dipalladium(II) as catalyst.

Yield: 88.9% of butyl cinnamate (GC analysis).

COMPARATIVE EXAMPLE 6

20 mmol of bromobenzene, 25 mmol of n-butyl acrylate and 25 mmol of potassium carbonate are stirred for 2 hours at 140° C. in 20 ml of dimethylacetamide with 2.0 μmol of palladium acetate as catalyst.

Yield: 70.8% of butyl cinnamate (GC analysis).

EXAMPLE 5

20 mmol of bromobenzene, 25 mmol of n-butyl acrylate and 25 mmol of potassium carbonate are stirred for 2 hours at 140° C. in 20 ml of dimethylacetamide with 1.0 μmol of di-μ-chloro-bis[2-[bis(1,1-dimethylethyl)phosphino]-2-methylpropyl-C,P]dipalladium(II) as catalyst.

Yield: 97.2% of butyl cinnamate (GC analysis).

EXAMPLE 6

20 mmol of bromobenzene, 25 mmol of n-butyl acrylate and 25 mmol of potassium carbonate are stirred for 2 hours at 140° C. in 20 ml of dimethylacetamide with 1.0 μmol of di-μ-acetato-bis[2-[bis(1,1-dimethylethyl)phosphino]-2-methylpropyl-C,P]dipalladium (II) as catalyst.

Yield: 95.0% of butyl cinnamate (GC analysis).

COMPARATIVE EXAMPLE 7

32 mmol of 4-bromoacetophenone, 35 mmol of n-butyl acrylate and 35 mmol of sodium acetate are stirred for 48 hours at 140° C. in 25 ml of dimethylacetamide.

Yield: 0% of n-butyl 4-acetylcinnamate (GC analysis).

EXAMPLE 7

32 mmol of 4-bromoacetophenone, 35 mmol of n-butyl acrylate and 35 mmol of sodium acetate are stirred for 48 hours at 140° C. in 25 ml of dimethylacetamide with 0.0016 μmol of di-μ-acetato-bis[2-[bis(1,1-dimethylethyl)phosphino]-2-methylpropyl-C,P]dipalladium(II) as catalyst.

Yield: 98.8% of n-butyl 4-acetylcinnamate (GC analysis).

EXAMPLE 8

20 mmol of chlorobenzene, 25 mmol of n-butyl acrylate, 2 mmol of lithium bromide and 25 mmol of potassium carbonate are stirred for 16 hours at 140° C. in 20 ml of dimethylacetamide with 0.1 mmol of di-μ-acetato-bis[2-[bis(1,1-dimethylethyl)phosphino]-2-methylpropyl-C,P]dipalladium(II) as catalyst.

Yield: 88.5% of butyl cinnamate (GC analysis)

The following commercial products were used:

Celite®/Aldrich Filter aid based on $SiO_2$

What is claimed is:

1. A process for preparing aromatic olefins of the formula (I)

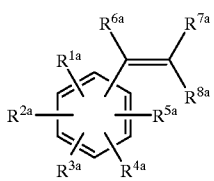
(I)

wherein $R^{1a}$ to $R^{5a}$ are, independently of one another, hydrogen, $C_1$–$C_8$-alkyl, $C_1$–$C_8$-alkoxy, $C_1$–$C_8$-acyloxy, O-phenyl, phenyl, fluorine, chlorine, bromine, OH, $NO_2$, $OSO_2CF_3$, CN, COOH, CHO, $SO_3H$, $SO_2R$, SOR, $NH_2$, NH—$C_1$–$C_8$-alkyl, N($C_1$–$C_8$-alkyl)$_2$, $CHal_3$, NHCO—$C_1$–$C_4$-alkyl, N—$C_1$–$C_4$-alkyl-CO—$C_1$–$C_4$-alkyl, COO—$C_1$–$C_8$-alkyl, $CONH_2$, CO—$C_1$–$C_8$-alkyl, NHCOH, NCOO—$C_1$–$C_4$-alkyl, CO-phenyl, COO-phenyl, CHCH—$CO_2$—$C_1$–$C_8$-alkyl, $CHCHCO_2H$, PO(phenyl)$_2$, PO($C_1$–$C_4$-alkyl)$_2$, $OSO_2$-phenyl or $OSO_2CH_3$, wherein one of the radicals $R^{1a}$ to $R^{5a}$ can also be

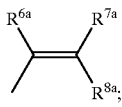

wherein $R^{6a}$ is hydrogen, $C_1$–$C_8$-alkyl, phenyl, O—$C_1$–$C_8$-alkyl or fluorines; and $R^{7a}$ and $R^{8a}$ are, independently of one another, hydrogen, CN, $CO_2H$, $CO_2$—$C_1$–$C_8$-alkyl, $CONH_2$, CONH—$C_1$–$C_4$-alkyl, CON($C_1$–$C_4$-alkyl)$_2$, fluorine, $CO_2$-phenyl, $C_1$–$C_8$-phenyl, PO(phenyl)$_2$, PO($C_1$–$C_4$-alkyl)$_2$, CO-phenyl, CO—$C_1$–$C_4$-alkyl, O—$C_1$–$C_4$-alkyl, NH—$C_1$–$C_4$-alkyl, $PO_3H$, $SO_3H$, $SO_3$—$C_1$–$C_4$-alkyl, $SO_2$—$C_1$–$C_4$-alkyl, O-phenyl or $C_1$–$C_8$-alkyl, by reacting haloaromatics of the formula (II)

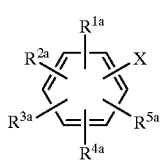
(II)

with olefins of the formula (III)

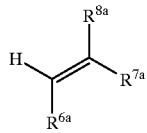
(III)

wherein $R^{1a}$ to $R^{8a}$ are as defined above and X is as defined for $R^{1a}$ to $R^{5a}$, wherein a palladium compound of the formula (IV)

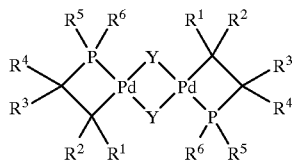
IV wherein $R^1$, $R^2$ are, independently of one another, hydrogen, $C_1$–$C_4$-alkyl, $C_3$–$C_{12}$-cycloalkyl, $C_1$–$C_4$-alkoxy, fluorine, N($C_1$–$C_4$-alkyl)$_2$, $CO_2$—$C_1$–$C_4$-alkyl, OCO—$C_1$–$C_4$-alkyl or aryl; and $R^3$, $R^4$, $R^5$, $R^6$ are, independently of one another, $C_1$–$C_8$-alkyl, $C_3$–$C_{12}$-cycloalkyl or aryl;

or wherein $R^1$ and $R^2$, $R^1$ or $R^2$ and $R^3$ or $R^4$, $R^3$ and $R^4$, $R^3$ or $R^4$ and $R^5$ or $R^6$, $R^5$ and $R^6$ together form an aliphatic ring having from 4 to 10 carbon atoms, or wherein $R^5$ and $R^6$, $R^3$ or $R^4$ and $R^5$ or $R^6$ together form an aromatic ring having from 5 to 9 carbon atoms, and Y is an anion of an inorganic or organic acid, is used as catalyst.

2. The process as claimed in claim 1, wherein, in formula (IV), $R^1$, $R^2$ are, independently of one another, phenyl, and $R^5$, $R^6$ are, independently of one another, phenyl, naphthyl, or anthracenyl which may each be substituted by from 1 to 3 $C_1$–$C_4$-alkyl or from 1 to 3 $C_1$–$C_4$-alkoxy groups, and Y is acetate, propionate, benzoate, chloride, bromide, iodide, fluoride, sulfate, hydrogensulfate, nitrate, phosphate, tosylate, mesylate, trifluoromethanesulfonate, tetrafluoroborate, acetylacetonate, hexafluoroacetylacetonate or pyrazolyl.

3. The process as claimed in claim 1, wherein, in formula (IV), $R^5$, $R^6$ are, independently of one another, o-trifluoromethylphenyl, o-trifluoromethyl-p-tolyl, o-trifluoromethyl-p-methoxyphenyl, o-methoxyphenyl, o,p-dimethoxyphenyl, o,o,p-trimethoxyphenyl, anthracenyl, tert-butyl, n-butyl, isopropyl, isobutyl, cyclohexyl or, 1-methylcyclohexyl.

4. The process as claimed in claim 1, wherein the catalyst used is di-μ-acetato-bis[2-[bis(1,1-dimethylethyl)phosphino]-2-methylpropyl-C,P]dipalladium(II), di-μ-acetato-bis[2-[(1,1-dimethylethyl)phenylphosphino]-2-methylpropyl-C,P]dipalladium(II), di-μ-chloro-bis[2-[bis(1,1-dimethylethyl)phosphino]-2-methylpropyl-C,P]dipalladium(II), di-μ-chloro-bis[2-[(1,1-dimethylethyl)phenylphosphino]-2-methylpropyl-C,P]dipalladium(II), di-μ-bromo-bis[2-[bis(1,1-dimethylethyl)phosphino]-2-methylpropyl-C,P]dipalladium(II) or di-µ-bromo-bis[2-[(1,1-dimethylethyl)phenylphosphino]-2-methylpropyl-C,P]dipalladium(II).

5. The process as claimed in claim 1, wherein the catalyst is prepared in situ.

6. The process as claimed in claim 1 is further carried out in the presence of dipolar aprotic solvents.

7. The process as claimed in claim 6, wherein said solvents are dialkyl sulfoxides, N,N-dialkylamides and/or alkylated lactams.

8. The process as claimed in claim 6, wherein said solvents are dimethyl sulfoxide, dimethylacetamide, dimethylformamide and/or N-methylpyrrolidone.

9. The process as claimed in claim 1, wherein the reaction is carried out at temperatures of from 20 to 200° C.

10. The process as claimed in claim 9, wherein the reaction is carried out at temperatures of from 60 to 180° C.

11. The process as claimed in claim 9, wherein the reaction is carried out at temperatures of from 80 to 150° C.

12. The process as claimed in claim 1, wherein acid HX formed in the reaction is neutralized by addition of a base.

13. The process as claimed in claim 12, wherein the base is an amine or an alkali metal or alkaline earth metal salt of a weak acid.

14. The process as claimed in claim 12, wherein the base is an alkylamine, carbonate, hydrogencarbonate or hydroxide, oxide or acetate of lithium, sodium, potassium, calcium or magnesium.

15. The process as claimed in claim 1, further comprises adding halides and pseudo halides of the alkali metals, alkaline earth metals or metals of transition groups VI to VIII.

16. The process as claimed in claim 1, further comprises adding trialkylammonium, tetraalkylammonium, trialkylphosphonium, tetraalkylphosphonium, trialkylarsonium or tetraalkylarsonium salts.

* * * * *